(12) United States Patent
Taylor et al.

(10) Patent No.: US 11,723,793 B2
(45) Date of Patent: *Aug. 15, 2023

(54) THERMAL TRANSFER DEVICE FOR PROVIDING THERMAL TREATMENT TO A PATIENT

(71) Applicant: Stryker Corporation, Kalamazoo, MI (US)

(72) Inventors: Gregory S. Taylor, Kalamazoo, MI (US); Ryan Ross, New Carlisle, IN (US)

(73) Assignee: Stryker Corporation, Kalamazoo, MI (US)

( * ) Notice: Subject to any disclaimer, the term of this patent is extended or adjusted under 35 U.S.C. 154(b) by 82 days.

This patent is subject to a terminal disclaimer.

(21) Appl. No.: 17/559,292

(22) Filed: Dec. 22, 2021

(65) Prior Publication Data

US 2022/0110784 A1 Apr. 14, 2022

Related U.S. Application Data

(63) Continuation of application No. 16/220,586, filed on Dec. 14, 2018, now Pat. No. 11,246,746.

(Continued)

(51) Int. Cl.
*A61F 7/00* (2006.01)
*A61F 7/08* (2006.01)
(Continued)

(52) U.S. Cl.
CPC .......... *A61F 7/0053* (2013.01); *A61F 7/0085* (2013.01); *A61F 7/0097* (2013.01);
(Continued)

(58) Field of Classification Search
CPC ...... A61F 2007/0054; A61F 2007/0295; A61F 2007/0298; A61F 7/0085
See application file for complete search history.

(56) References Cited

U.S. PATENT DOCUMENTS

| 5,146,932 A | 9/1992 | McCabe |
| 5,448,788 A | 9/1995 | Wu |

(Continued)

FOREIGN PATENT DOCUMENTS

| CN | 201091396 Y | 7/2008 |
| CN | 105054666 A | 11/2015 |

OTHER PUBLICATIONS

English language abstract and machine-assisted English translation for CN 201091396 extracted from espacenet.com database on Feb. 13, 2019, 9 pages.

(Continued)

*Primary Examiner* — Tigist S Demie
(74) *Attorney, Agent, or Firm* — Howard & Howard Attorneys PLLC (57) ABSTRACT

A thermal transfer device for providing thermal treatment to a patient. A patient support portion supporting and contacting the patient includes a first segment of a fluid flow path to receive a fluid from a fluid source. A flexible covering coupled and movable relative to the patient support portion defines a space therebetween that substantially conforms to the patient. The flexible covering includes a second segment of the fluid flow path. The fluid is circulated through an inlet, an outlet, and fluid flow path for supplying heat to or removing heat from the patient support portion and the flexible covering. A fluid circulation system with a controller may selectively adjust heat transfer from temperature zones defining the patient support portion. The thermal transfer device or a mattress cover may provide for controlling the microclimate, or conditions at or near the interface between the patient and the patient support portion.

19 Claims, 8 Drawing Sheets

Related U.S. Application Data (60) Provisional application No. 62/609,036, filed on Dec. 21, 2017.

(51) Int. Cl.
*A61G 7/05* (2006.01)
*A61F 7/02* (2006.01)

(52) U.S. Cl.
CPC .................. *A61F 7/08* (2013.01); *A61G 7/05* (2013.01); *A61F 2007/0054* (2013.01); *A61F 2007/0093* (2013.01); *A61F 2007/0094* (2013.01); *A61F 2007/0095* (2013.01); *A61F 2007/0096* (2013.01); *A61F 2007/0295* (2013.01); *A61F 2007/0298* (2013.01); *A61G 2210/70* (2013.01); *A61G 2210/90* (2013.01)

(56) References Cited

U.S. PATENT DOCUMENTS

| | | |
|---|---|---|
| 5,800,480 A | 9/1998 | Augustine et al. |
| 6,123,716 A | 9/2000 | Augustine et al. |
| 6,210,427 B1 | 4/2001 | Augustine et al. |
| 6,228,106 B1 | 5/2001 | Simbruner et al. |
| 6,245,096 B1 | 6/2001 | Tomic-Edgar et al. |
| 6,354,099 B1 | 3/2002 | Bieberich |
| 7,056,282 B2 | 6/2006 | Chester et al. |
| 7,555,792 B2 | 7/2009 | Heaton et al. |
| 8,191,187 B2 | 6/2012 | Brykalski et al. |
| 8,308,785 B2 | 11/2012 | Pierre et al. |
| 8,332,975 B2 | 12/2012 | Brykalski et al. |
| 8,914,924 B2 | 12/2014 | Stryker et al. |
| 9,089,462 B1 | 7/2015 | Lafleche |
| 9,131,781 B2 | 9/2015 | Zaiss et al. |
| 2009/0312823 A1 | 12/2009 | Patience et al. |
| 2011/0092890 A1 | 4/2011 | Stryker et al. |
| 2011/0238143 A1* | 9/2011 | Schock ............... A61F 7/0053 607/104 |
| 2019/0192337 A1 | 6/2019 | Taylor et al. |

OTHER PUBLICATIONS

English language abstract and machine-assisted English translation for CN 105054666 extracted from espacenet.com database on Feb. 13, 2019, 9 pages.

Gaymar Industries Inc., "Mul-T Blankets/Medi-Therm III Brochure", 2006, 2 pages.

Stryker Medical, "Altrix Precision Temperature Management System", 2016, 8 pages.

\* cited by examiner

THERMAL TRANSFER DEVICE FOR PROVIDING THERMAL TREATMENT TO A PATIENT

CROSS-REFERENCE TO RELATED APPLICATIONS

The subject patent application is a Continuation of U.S. patent application Ser. No. 16/220,586, filed on Dec. 14, 2018, which claims priority to and all the benefits of U.S. Provisional Patent Application No. 62/609,036, filed on Dec. 21, 2017, the disclosures of each of which are hereby incorporated by reference in their entirety.

BACKGROUND

The facilitation of patient temperature management in a health care setting often includes providing thermal treatment to the patient. Thermal treatment may be clinically indicated to regulate or maintain core body temperature of the patient, administer localized therapy to a portion of the patient anatomy, provide for patient comfort, and the like. Perhaps the most well-known thermal transfer device for thermal treatment is the electric blanket. The electric blanket is often cumbersome and fails to sufficiently conform to the anatomy of the patient for optimal heat transfer. Further, the size of the electric blanket often obstructs visualization of and prevents access to the anatomy proximate to that receiving the thermal treatment, anatomy which may be of interest to treating medical professionals.

Another known thermal transfer device is a removable sleeve through which a fluid line routes hot or cold fluid to heat or cool the patient anatomy around which the sleeve is wrapped. The sleeve includes an inlet to receive a fluid line from a fluid source, and an outlet to receive another fluid line for expelling expended fluid. Often during thermal treatment multiple sleeves are utilized simultaneously, for example, around the bilateral upper and lower extremities of the patient, and the torso of the patient. In such an example, upwards of ten fluid lines may be coupled to the patient and to a console positioned adjacent a patient support apparatus supporting the patient. The substantial number of fluid lines makes decoupling and recoupling the thermal transfer device(s) laborious and cumbersome, and their presence about the patient support apparatus significantly hinders maneuverability of treating medical professionals.

Furthermore, the patient support apparatus, such as a hospital bed with a mattress, has evolved to include elaborate systems to control the conditions at or near an interface between a cover of the mattress and skin of the patient. The ability to affect or control the conditions at the interface is often referred to as providing a "microclimate," with temperature and humidity being conditions of particular interest. Controlling the temperature and humidity at the skin of the patient is one aspect of patient temperature management. Systems for providing the optimal microclimate have yet to be fully realized.

Therefore, a need exists in the art for a thermal transfer device and patient temperature management system designed to overcome one or more of the aforementioned disadvantages.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
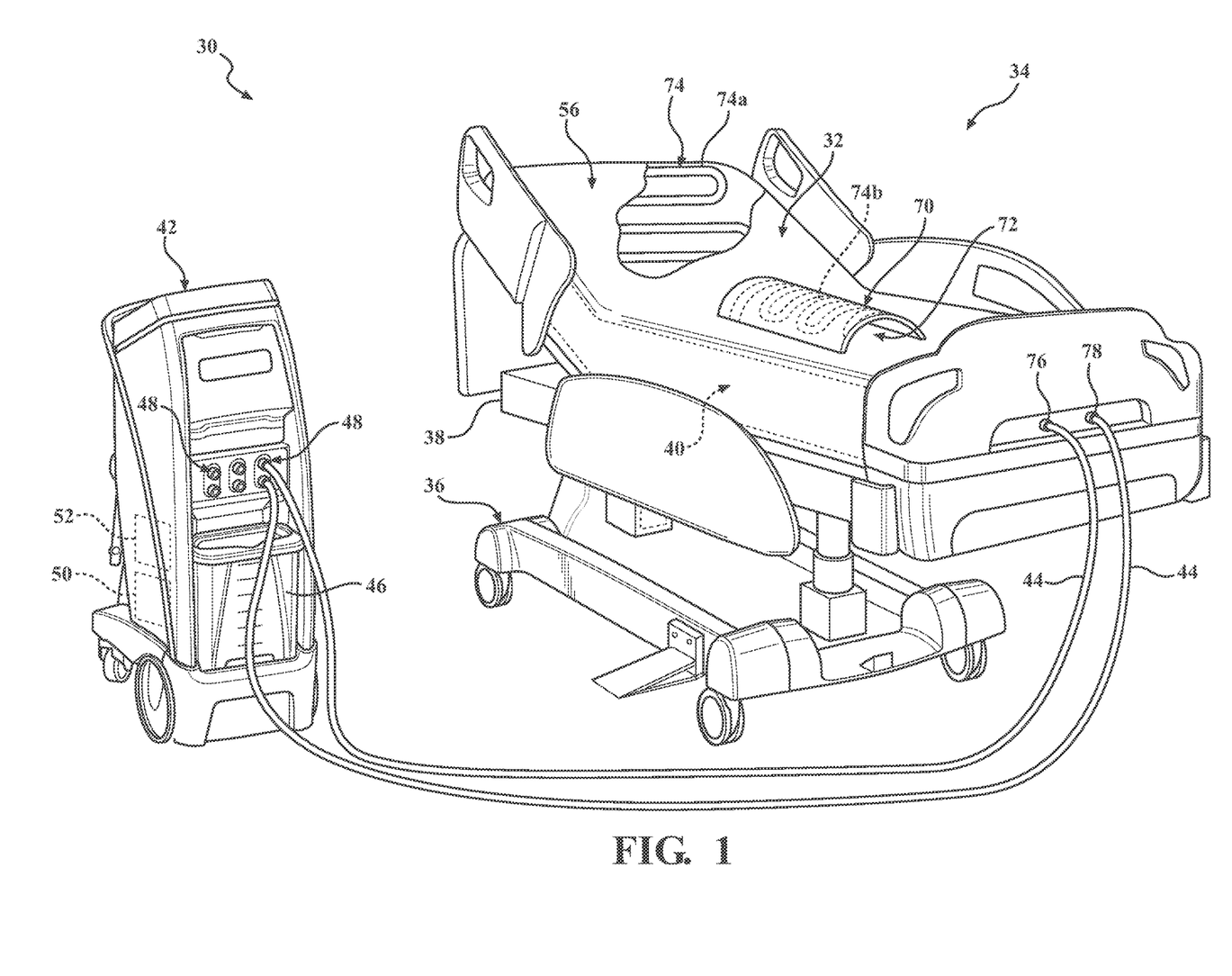
FIG. 1 is a perspective view of a patient temperature management system including a thermal transfer device in accordance with an exemplary embodiment of the present disclosure for providing thermal treatment to a patient supported on a patient support apparatus.

FIG. 1 illustrates a patient temperature management system 30 including a thermal transfer device 32 in accordance with an exemplary embodiment of the present disclosure. The thermal transfer device 32 of the patient temperature management system 30 provides thermal treatment to a patient P (see FIG. 2) supported on a patient support apparatus 34. The patient support apparatus 34 may include a base 36 adapted to rest upon a floor surface, and a patient support deck 38 coupled to the base 36. In certain embodiments to be described, the patient support apparatus 34 includes a mattress 40 coupled to or supported on the patient support deck 38. The patient support apparatus 34 shown in FIG. 1 is a hospital bed, but alternatively may be a stretcher, cot, trolley, gurney, wheelchair, or suitable support or transport apparatus.

The patient temperature management system 30 may include a console 42 adapted to regulate fluid temperature and circulate the heated or cooled fluid through the thermal transfer device 32 to be described. The console 42 is coupled to the thermal transfer device 32 with hoses 44. The console 42 may comprise a fluid reservoir that functions as a fluid source 46 for the thermal transfer device 32. The console 42 may comprise a pair of ports 48 adapted to receive the hoses 44 with the pair of ports 48 including an inlet port and an outlet port. The hoses 44 include, for example, Colder-style or Clik-Tite connections for coupling to the ports 48. The ports 48 are in fluid communication with the fluid source 46 such that, when the hoses 44 are coupled to the ports 48, the hoses 44 are in fluid communication with the fluid source 46. FIG. 1 shows the console 42 including three pairs of ports 48, but any number of pairs of ports 48 are contemplated. The console 42 further includes a pump 50, an internal fluid circuit (not shown), and an energy transfer system 52. The pump 50 moves the fluid within the fluid circuit during which the energy transfer system 52 either supplies or removes heat from the fluid. Once the fluid is sufficiently heated or cooled (also referred to herein as "conditioned"), the pump 50 moves the conditioned fluid through the hoses 44 to the thermal transfer device 32 to provide the thermal treatment to the patient P in a manner to be described. One exemplary console suitable for operation with the thermal transfer device 32 of the present disclosure is the Altrix™ Model 8001 Precision Temperature Management System produced by Stryker Corporation (Kalamazoo, Mich.).

Figure 2:
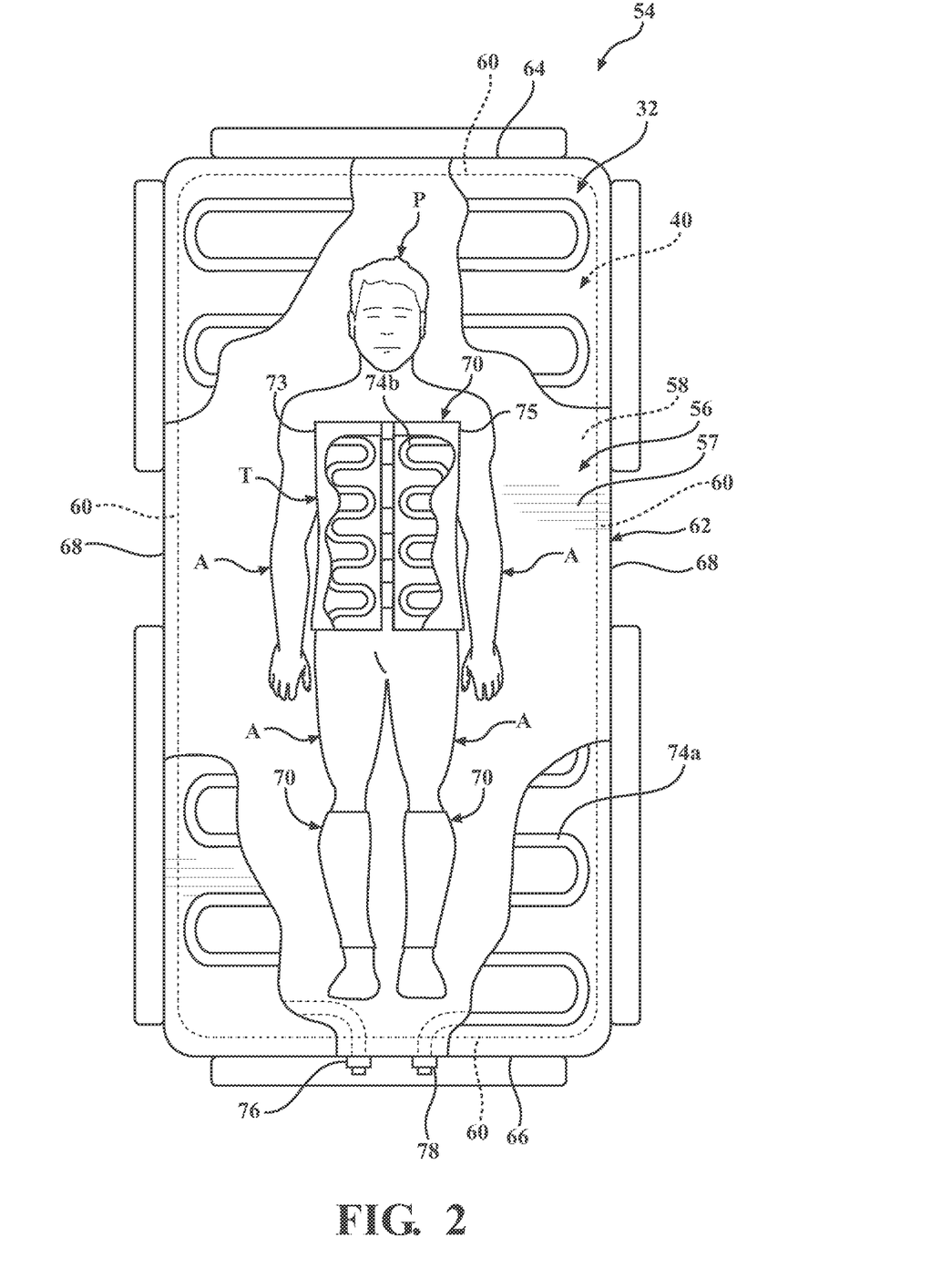
FIG. 2 is a plan view of the thermal transfer device in accordance with another exemplary embodiment of the present disclosure with the patient supported on a patient support portion of the thermal transfer device.

With concurrent reference to FIG. 2 showing the patient P supported in the supine position on the patient support apparatus 34, the thermal transfer device 32 comprises a patient support portion 56 adapted to support and contact the patient P requiring the thermal treatment. In one exemplary embodiment, the patient support portion 56 comprises a flexible layer 57 removably coupled to and substantially conforming to at least a portion of the mattress 40 of the patient support apparatus 34. In certain embodiments, the flexible layer 57 may cover an entirety of an upper surface 58 of the mattress 40 defined between pairs of opposing sides 60 of the mattress 40. The flexible layer 57 of the thermal transfer device 32 may extend along a portion or an entirety of the opposing sides of the mattress 40. For example, the thermal transfer device 32 may include fasteners 59, such as elastic features coupled to or embedded within concertinaed fabric (see FIG. 3), adapted to resiliently secure the flexible layer 57 of the thermal transfer device 32 to the mattress 40. Other suitable fasteners include zippers, hook and eye connections, buttons, snaps, and the like. It is contemplated that in certain embodiments, the thermal transfer device 32 may substantially encase the mattress 40 or another mattress pad (e.g., a mattress overlay or mattress topper) situated on the patient support deck 38 or the mattress 40.

The patient support portion 56 comprises an outer periphery 62 sized so that a majority of the patient P is supported on the patient support portion 56 within the outer periphery 62 during use, as shown in FIG. 2. FIG. 2 shows an entirety of the patient P supported within the outer periphery 62 of the patient support portion 56. The outer periphery 62 may be defined, at least in part, by a head end 64, a foot end 66, and opposing sides 68 extending between the head end 64 and the foot end 66. In other words, the outer periphery 62 may be considered a perimeter of the patient support portion 56 adapted to support and contact the patient P.

The thermal transfer device 32 further includes a flexible covering 70 coupled to the patient support portion 56. In a manner to be described, the flexible covering 70 is movable relative to the patient support portion 56 to define a space 72 therebetween (see FIG. 1). The space 72 receives and substantially conforms to a portion of the patient P to, among other advantages, maximize the contact area between the flexible covering 70 and the patient P during the thermal treatment.

The thermal transfer device 32 includes a fluid flow path, referenced generally as 74. The fluid flow path 74 receives fluid from the fluid source 46, such as the reservoir of the console 42, typically subsequent to the fluid being conditioned. The thermal transfer device 32 further includes an inlet 76 and an outlet 78. The inlet 76 and the outlet 78 are in communication with the fluid flow path 74 of the thermal transfer device 32. The inlet 76 and the outlet 78 are adapted to receive the hoses 44 coupled at an end opposite to the console 42. The inlet 76 and the outlet 78 may be coupled with the hoses 44 via, for example, the Colder-style or Clik-Tite connections. When the hoses 44 are coupled to the inlet 76 and the outlet 78 (and the console 42), the fluid flow path 74 of the thermal transfer device 32 is in fluid communication with the fluid source 46. The inlet 76 and the outlet 78 are arranged to circulate the fluid from the fluid source 46 through the fluid flow path 74 to supply heat or remove heat from the patient support portion 56 and the flexible covering 70. The pump 50 of the console 42 may provide the motive power to circulate the fluid through the fluid flow path 74.

In the exemplary embodiment of the thermal transfer device 32 illustrated in FIGS. 1 and 2, the fluid flow path 74 is arranged in a tortuous manner when viewed in plan. In other words, the fluid flow path 74 may assume an exaggerated curvilinear path designed to maximize heat transfer between the thermal transfer device 32 and the patient P. In certain embodiments to be described, the fluid flow path 74 may be disposed within the flexible layer 57 with the fluid flow path 74 defined by a channel system secondary to radiofrequency (RF) welding of adjacent pieces of material during assembly of the flexible layer 57 and the flexible covering 70. Alternatively, the fluid flow path 74 may be defined by discrete tubing disposed within the flexible layer 57 and the flexible covering 70.

The fluid flow path 74 comprises a first segment 74a and a second segment 74b. The first segment 74a is associated with the patient support portion 56, and the second segment 74b is associated with the flexible covering 70. In one example, the first segment 74a is coupled to the flexible layer 57, and the second segment 74b is coupled to the flexible covering 70. The first and second segments 74a, 74b are in fluid communication with one another and with the inlet 76 and the outlet 78 of the thermal transfer device 32. In other words, heated and cooled fluid provided by the console 42 supplies and removes heat, respectively, from both the patient support portion 56 and the flexible covering 70 with fewer hoses (e.g., two hoses) being required than a patient temperature management system. For example, the conditioned fluid may be circulated through both the patient support portion 56 and the flexible covering 70 via a singular inlet and a singular outlet (e.g., the inlet 76 and the outlet 78). The inlet 76 and the outlet 78 may be positioned at the foot end 66, as shown in FIGS. 1 and 2, or at the head end 64 or the opposing sides 68. In another exemplary embodiment, the thermal transfer device 32 includes one or more auxiliary ports (e.g., an inlet for receiving a hose or other external fluid line) for providing the conditioned fluid to the flexible covering 70. In embodiments where auxiliary ports are provided, the ports are coupled to the patient support portion 56 at or near the head end 64, the foot end 66, and/or the opposing sides 68 of the patient support portion 56 such that the coupled hoses are positioned away from the patient P.

In certain embodiments, the first and second segments 74a, 74b of the fluid flow path 74 are continuous. The fluid moves between the first and second segments 74a, 74b in a generally steady-state manner without significant impediment at the interface 80 between the patient support portion 56 and the flexible covering 70 (see FIGS. 3, 4A and 4B). In certain embodiments, the second segment 74b of the fluid flow path 74 may be devoid of a port such that an entirety of the fluid within the second segment 74b either has been or will be circulated through the first segment 74a before returning to the console 42 for further conditioning. Consequently, the flexible covering 70 substantially conforming to the patient comfortably and effectively provides the thermal treatment without requiring the auxiliary ports (e.g., in addition to the inlet 76 and the outlet 78). The reduced number of hoses 44 renders coupling and decoupling the thermal transfer devices 32 less laborious and cumbersome, and maneuverability of treating medical professionals about the patient support apparatus 34 is drastically improved. Coupling the hoses 44 at the foot end 66 and correspondingly positioning the console 42 may further improve maneuverability about the patient support apparatus 34.

Figure 3:
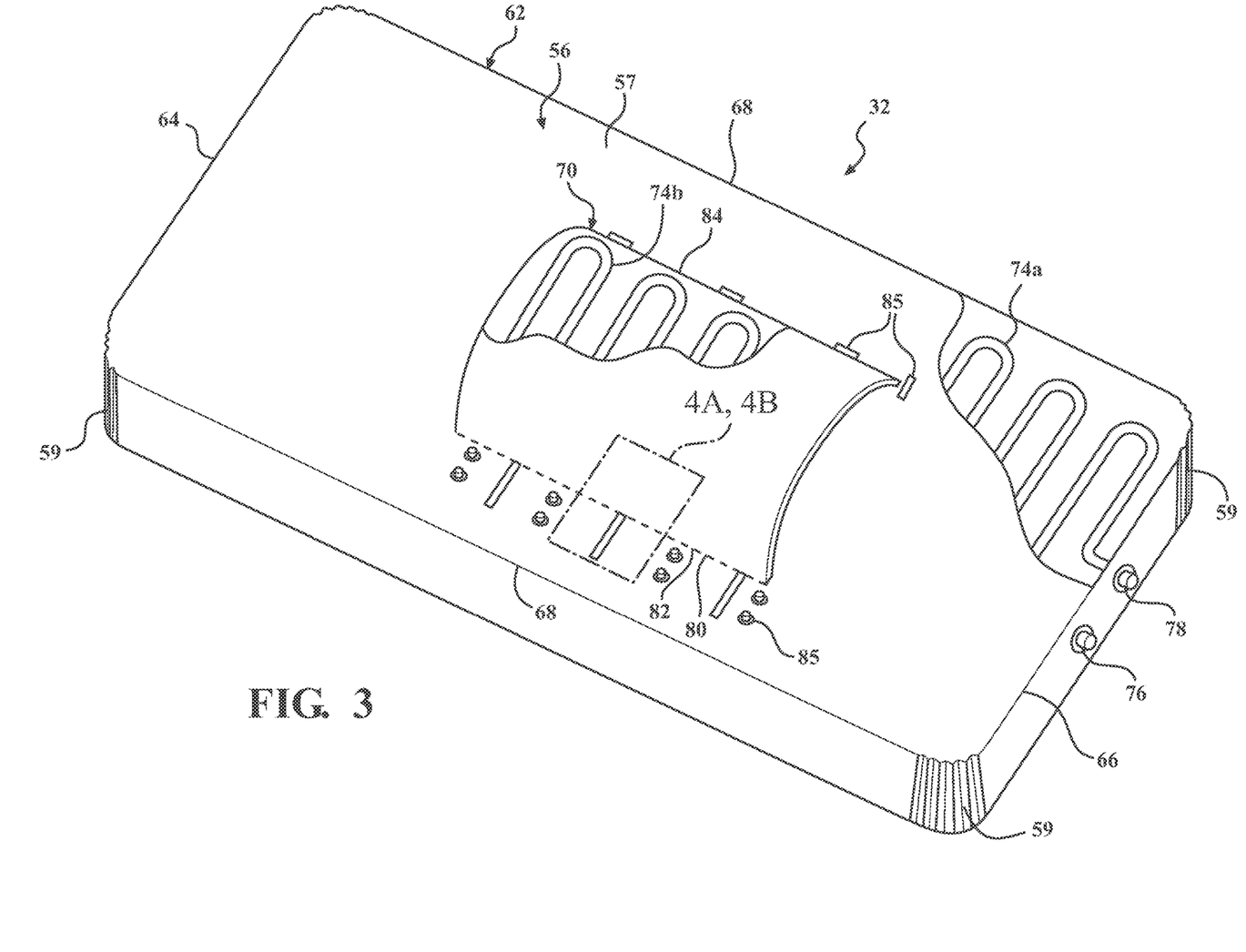
FIG. 3 is a perspective view of the thermal transfer device of FIG. 1.

For illustrative purposes, FIGS. 1 and 3 show one flexible covering 70 occupying a significant area of the patient support portion 56. It is to be understood that the thermal transfer device 32 may include any number, size, and/or shape of flexible coverings 70. For example, the thermal transfer device 32 of FIG. 2 includes three flexible coverings 70, one of which defines the space 72 (see FIG. 1) adapted to receive and substantially conform to the torso T of the patient, and two of which each define the space 72 adapted to receive and substantially conform to appendages A of the patient P (e.g., the upper extremities and/or the lower extremities) extending from the torso T. FIG. 2 shows the torso T of the patient P being received within the space 72 provided by the flexible covering 70 comprising a pair of flexible coverings 73 detachably coupled to one another with fasteners such as zippers, hook and eye connections, buttons, snaps, adhesive, and the like. The fasteners may be positioned adjacent the patient P generally opposite the patient support portion 56 (i.e., a center of the torso T) to provide for ease with coupling and decoupling the thermal transfer device 32 to and from the patient P. Each of the pair of flexible coverings 73 may comprise the second segment 74b of the fluid flow path 74 operating in a manner described throughout the present disclosure.

Referring to FIG. 3, the thermal transfer device 32 in accordance with one exemplary embodiment is shown. The thermal transfer device 32 includes the patient support portion 56 having the outer periphery 62 sized so that a majority of the patient P is supported on the patient support portion 56 within the outer periphery 62 during use. The flexible layer 57 comprises the patient support portion 56 with the flexible layer 57 adapted to be removably coupled to the mattress 40. For example, the flexible layer 57 may be formed from fabric (e.g., a cotton-elastane blend) adapted to substantially conform to at least a portion of the mattress 40 and provide comfort to the patient P disposed thereon. The fasteners 59 are positioned at each of the four corners with the fasteners 59 adapted to be stretched over a corresponding corner of the mattress 40 to resiliently secured the thermal transfer device 32 to the mattress 40.

The flexible covering 70 is coupled to the patient support portion 56. A portion of the flexible covering 70 may be fixedly coupled to the patient support portion 56. For example, FIG. 3 shows the flexible covering 70 at least partially defined between a first end 82 opposite a second end 84 with the first end 82 coupled to the patient support portion 56 to define the interface 80. The flexible covering 70 may be fixedly coupled to the patient support portion 56 through sewing, ultrasonic or RF welding, and the like, such that the first end 82 is stationary relative to the patient support portion 56. Alternatively, the first end 82 of the flexible covering 70 may be removably coupled to the patient support portion 56 through counterposing couplers, such as zippers, hook and eye connections, buttons, snaps, adhesive, and the like. The flexible covering 70 of the thermal transfer device 32 may be configurable between multiple configurations including the flexible covering 70 being coupled at one of several positions. For example, the patient support portion 56 may comprise rows of snaps arranged at certain positions with each row adapted to receive counterposing snaps coupled to the flexible covering 70 near the first end 82. The flexible covering 70 may be selectively positioned on the patient support portion 56 based on to which one of the rows of snaps the flexible covering 70 is coupled. In another example, the slots extend through the patient support portion 56 with T-shaped clips coupled near the first end 82 of the flexible covering 70 extending through the slots. The T-shaped clips may be slidably moved within the slots to selectively position the flexible covering 70 on the patient support portion 56. FIG. 3 shows schematic representations of the aforementioned examples for adjusting the position the flexible covering 70 on the patient support portion 56.

As mentioned, the flexible covering 70 is movable to the patient support portion 56 to define the space 72 therebetween (see FIG. 1). With reference to FIG. 3, the second end 84 of the flexible covering 70 may be freely manipulable by a user grasping the flexible covering 70. The flexible covering 70 is moved in a manner to substantially conform to a portion of the patient P (e.g., the appendage(s) A, the torso T, etc.) supported on the patient support portion 56, after which the flexible covering 70 may be coupled to the patient support portion 56 at or near the second end 84. FIG. 3 shows the flexible covering 70 adapted to be coupled to the patient support portion 56 at or near the second end 84 with fasteners 85 of hook and eye connections. Other suitable fasteners 85, including those previously mentioned, may be an alternative. Often, the first and second ends 82, 84 may utilize the same type of fasteners 85. Thus, in certain exemplary embodiments of the thermal transfer device 32, the fasteners 85 are disposed at each of the first and second ends 82, 84 with the fasteners 85 adapted to removably couple the first and second ends 82, 84 to the patient support portion 56.

With the flexible covering 70 substantially conforming to the portion of the patient P supported on the patient support portion 56, the resulting arrangement includes the thermal transfer device 32 substantially surrounding the portion of the patient P. With the torso T of the patient P as an example, the torso T is surrounded anteriorly and laterally by the flexible covering 70 and posteriorly by the patient support portion 56 on which the torso T is supported. Contact area between the thermal transfer device 32 and the torso T of the patient P is maximized to provide for optimal heat transfer during the thermal treatment to be described.

The thermal transfer device 32 advantageously maximizes the thermal communication between the fluid flow path 74 and the patient P. As mentioned, the first segment 74a of the fluid flow path 74 is associated with the patient support portion 56, and the second segment 74b of the fluid flow path 74 is associated with the flexible covering 70. In the exemplary embodiment of FIG. 3, the first segment 74a is coupled to the flexible layer 57, and the second segment 74b is coupled to the flexible covering 70 with both the first and second segments 74a, 74b in fluid communication with the inlet 76 and the outlet 78 as described. To provide fluid communication between the first and second segments 74a, 74b and the inlet 76 and the outlet 78, the fluid flow path 74 may be, for example, continuous across the interface 80 separating the flexible covering 70 and the patient support portion 56.

Figure 4A:
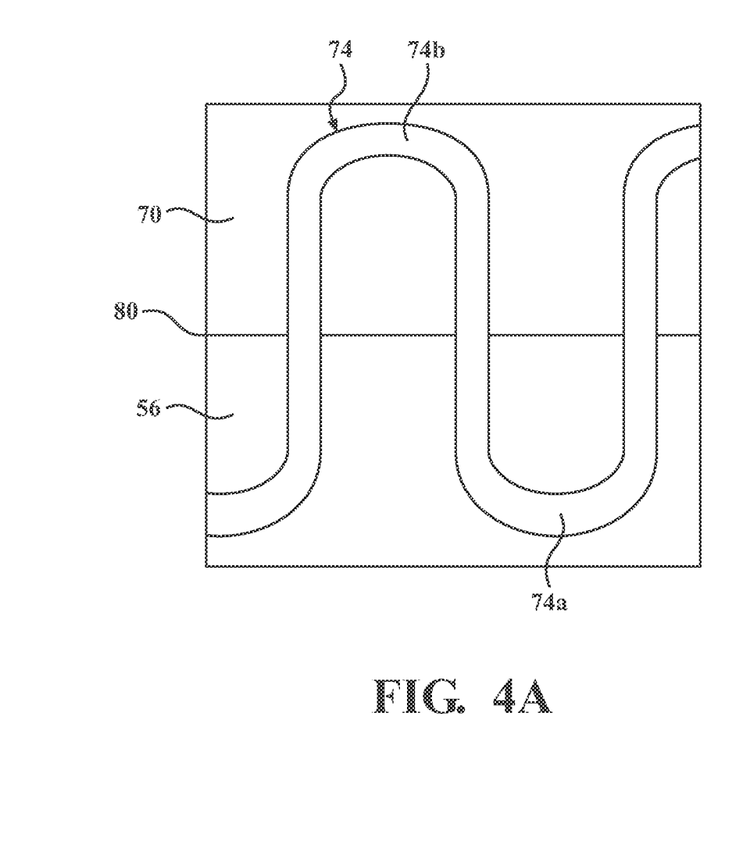
FIG. 4A is a detailed view of the thermal transfer device of FIG. 3 with a schematic representation of a portion of a fluid flow path in accordance with an exemplary embodiment of the present disclosure.
Figure 4B:
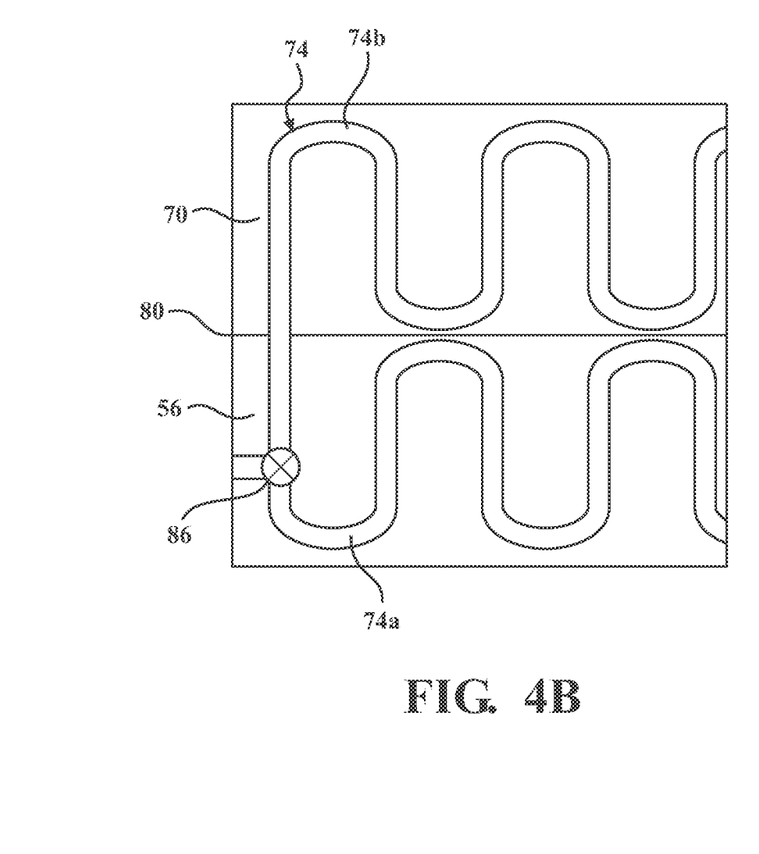
FIG. 4B is a detailed view of the thermal transfer device of FIG. 3 with a schematic representation of a portion of a fluid flow path in accordance with another exemplary embodiment of the present disclosure.

FIGS. 4A and 4B are detailed views with schematic representations of the fluid flow path 74 across the interface 80 separating the flexible covering 70 and the patient support portion 56. FIGS. 4A and 4B show two exemplary manners by which the fluid flow path 74 may provide conditioned fluid to both the patient support portion 56 and the flexible covering 70 without the need for auxiliary ports. In FIG. 4A, the first and second segments 74a, 74b may be considered continuous. In other words, fluid through a portion of the first segment 74a flows continuously to a portion to the second segment 74b. Stated differently, the tortuous path of the fluid flow path 74 extends through the interface 80 repeatedly such that the fluid moves through first and second segments 74a, 74b in an alternating fashion. In FIG. 4B, the first and second segments 74a, 74b are substantially separated on opposing sides of the interface 80 with the first and second segments 74a, 74b joined at a junction, such as a valve 86 with function to be described. The fluid may be bifurcated at the valve 86 with a portion of the fluid directed to the first segment 74a of the fluid flow path 74, and another portion of the fluid directed through the second segment 74b of the fluid flow path 74. The first and second segments 74a, 74b may be reunited at another junction, generally after the portion fluid has moved through the second segment 74b of the fluid flow path 74 associated with the flexible covering 70. Variations to the fluid flow path 74 providing conditioned fluid to both the patient support portion 56 and the flexible covering 70 are within the scope of the present disclosure.

It is to be understood that when the flexible covering 70 is substantially conforming to the patient P supported on the patient support portion 56, the patient P may be in thermal communication with both the first and second segments 74a, 74b of the fluid flow path 74. The area of the patient support portion 56 upon which the patient P is supported (and opposite the flexible covering 70) includes the first segment 74a of the fluid flow path 74. Thus, using the earlier example including the torso T of the patient P positioned supine on the patient support portion 56, the torso T is in thermal communication anteriorly and laterally with the second segment 74b of the fluid flow path 74, and in thermal communication posteriorly with the first segment 74a of the fluid flow path 74. Consequently, the thermal transfer device 32 may substantially surround the portion of the patient P to provide for optimal heat transfer during the thermal treatment.

Figure 5:
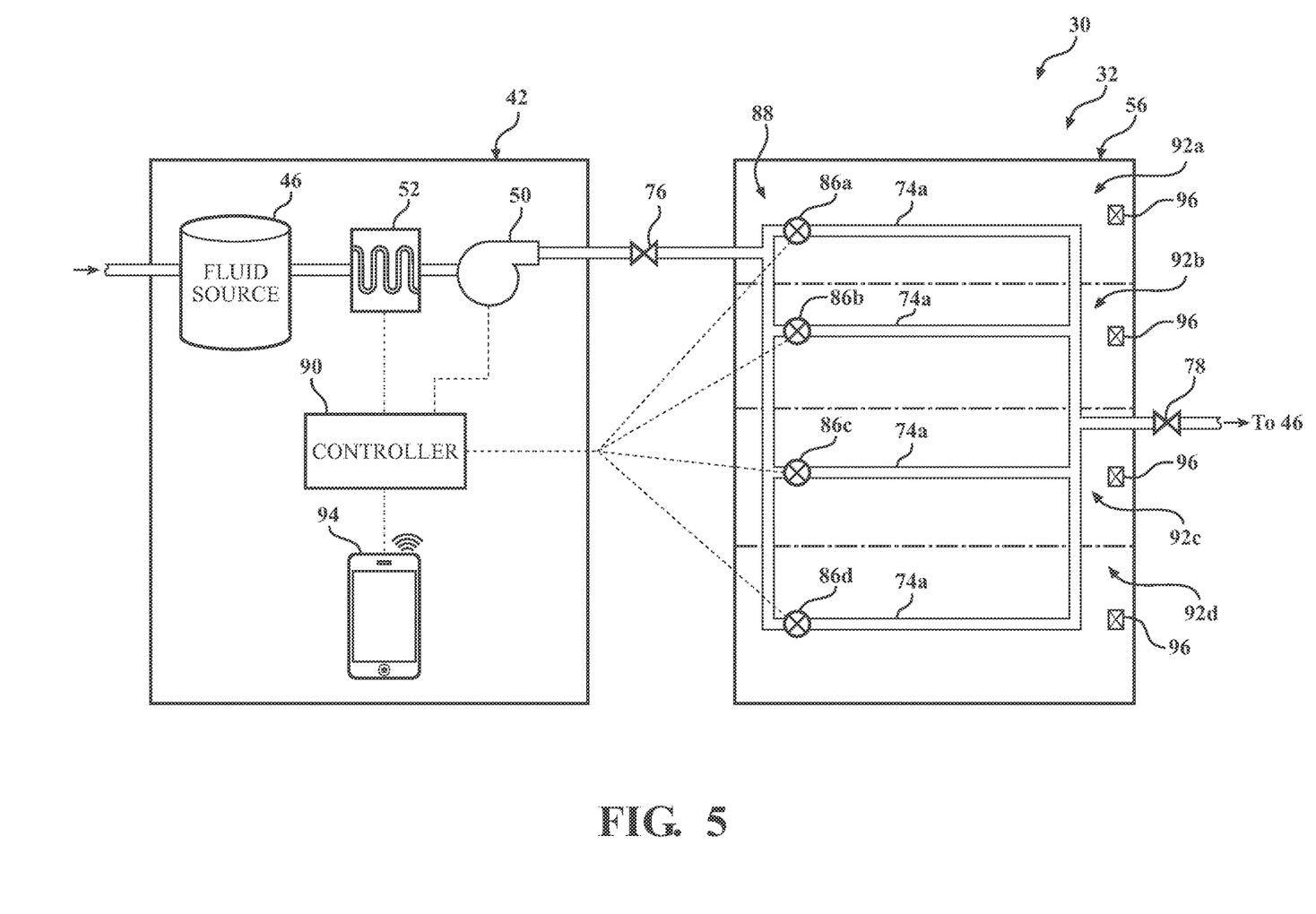
FIG. 5 is a schematic diagram of the patient temperature management system including the thermal transfer device.

The patient temperature management system 30 of the present disclosure further provides for improved control of the microclimate, in particular the conditions at or near an interface between the thermal transfer device 32 and the skin of the patient. Referring to FIG. 5, the thermal transfer device 32 of the patient temperature management system 30 includes a fluid circulation system 88 with valves 86, the fluid source 46, the pump 50, the energy transfer device 52, and a controller 90. In one exemplary embodiment, at least certain aspects of the fluid circulation system 88 are integrated into the console 42 previously described. The valves 86, the pump 50, and/or the energy transfer device 52 may be in electric communication with the controller 90. In manners to be described, the controller 90 operates the pump 50 and the valves 86 to circulate the fluid from the fluid source 46 through the fluid flow path 74, and the controller 90 operates the energy transfer device 52 to add or remove energy from the fluid, thereby altering the temperature of the fluid within the fluid flow path 74. It is contemplated that at least certain aspects of the fluid circulation system 88 may be integrated with the patient support apparatus 34.

The patient support portion 56 of FIG. 5 is represented schematically with the fluid flow path 74 divided into four branches each comprising a portion of the first segment 74a of the fluid flow path 74. In other words, FIG. 5 shows only the first segment 74a of the fluid flow path 74 for illustrative purposes to describe providing temperature zones 92a-92d defining the patient support portion 56. It is to be understood that the disclosure that follows may also be incorporated into the second segment 74b of the fluid flow path 74 associated with the flexible covering 70.

With the patient P supported on the patient support portion 56 and the flexible covering 70 coupled in a manner previously described, the conditioned fluid is circulated about the fluid circulation system 88 to provide the thermal treatment. In one exemplary embodiment, an input is provided to a user interface 94 to select certain parameters for the thermal treatment, including time, temperature, and humidity, among others. The controller 90 in communication with the user interface 94, either wired or wirelessly, receive the parameters and operates the pump 50, the energy transfer device 52, and/or the valves 86 in a suitable manner. The pump 50 moves the fluid from the fluid source 46 through the energy transfer device 52. The controller 90 operates the energy transfer device 52 to add or remove energy from the fluid, thereby adjusting the temperature of the fluid. The conditioned fluid is circulated through the inlet 76 and through one or more of the valves 86a-86d selectively operated by the controller 90. Within at least a portion of the fluid flow path 74 in thermal communication with the patient P, heat is removed from the conditioned fluid by the patient P having a lower body temperature than the conditioned fluid, or alternatively heat is removed from the patient P by the conditioned fluid having a lower temperature than the body temperature of the patient P. The expended fluid (i.e., the fluid following heat transfer to or from the patient P) is circulated through the outlet 78 and returned to either the fluid source 46 or the energy transfer device 52 to be reconditioned.

If, for example, it is desired to have substantially an entirety of the patient support portion 56 at one temperature, each of the valves 86a-86d associated with of the four branches of the fluid flow path 74 of FIG. 5 may be controlled by the controller 90 in a coordinated manner. The valves 86a-86d may be fully opened, after which the condition fluid flows through all four branches under substantially similar motive power from the pump 50. The volume flow rate of the conditioned fluid through each of the four braches the fluid flow path 74 is the same, and the heat transfer from each of the temperature zones 92a-92d defining the patient support portion 56 may be substantially the same.

Changing the amount of heat transfer from one or more of the temperature zones 92a-92d may be effectuated in any number of ways. The valves 86a, 86b may be opened or closed to any extent to restrict the volume flow rate of the conditioned fluid within the fluid flow path 74 to vary the heat supplied or heat removed from the temperature zones 92a-92d. It should be appreciated that other valves (not shown) may be provided to prevent the flow of fluid from one zone to another, such as additional control valves, check valves, and the like. The schematic illustration in FIG. 5 is merely an illustration and could be configured in numerous ways to provide the functions described herein. Additionally or alternatively, the controller 90 may operate the pump 50 to selectively adjust the volume flow rate of the conditioned fluid within the fluid flow path 74. Additionally or alternatively, the controller 90 may operate the energy transfer device 52 to selectively adjust the temperature of the conditioned fluid within the fluid flow path 74 to vary the heat supplied or heat removed from the temperature zones 92a-92d. The aforementioned means for changing the amount of heat transfer are applicable to operations in which the temperature of all of the temperature zones 92a-92d is substantially the same, as well as operations to be described in which the temperature between the temperature zones 92a-d is selectively varied.

If, for another example, it is desired to have more heat transfer in two of the temperature zones 92a, 92b than the other two of the temperature zones 92c, 92d, the controller 90 may operate the valves 86a-86d in a coordinated manner to selectively route the flow of the conditioned fluid within the fluid flow path 74. The valves 86a, 86b may be fully opened, and the valves 86c, 86d may be partially opened or closed. Relatively more of the conditioned fluid is routed to two of the temperature zones 92a, 92b, thereby providing more heat transfer in the corresponding area(s) of the patient support portion 56. It should be appreciated that the valves 86a, 86b, 86c, 86d could be opened and closed in short pulses (e.g. 1 second, 2 seconds, more, or less), such that only one of the valves 86a, 86b, 86c, 86d is open at any given time, but still accomplishing the desired temperature profiles. It is further contemplated that the fluid circulation system 88 may be designed such that one or more of the temperature zones 92a-92d extracts heat (i.e., cools the patient P or a "cool zone"), and the patient P extracts heat from another one or more of the temperature zones 92a-92d (i.e., warms the patient or a "hot zone"). In one example, the area of the patient support portion 56 contacting and supporting the torso T of the patient P is a cool zone to more effectively lower core body temperature, while the area of the patient support portion 56 contacting and supporting the appendages A of the patient P is a hot zone to reduce pressure ulcers or muscle cramping.

It is emphasized that the heat transfer provided by flexible covering 70 is also selectively controllable. In certain embodiments, one or more valves 86 may be disposed at or near the interface 80 between the patient support portion 56 and the flexible covering 70 (see, for example, FIG. 4B). The controller 90 may selectively open or close the valves 86 to any extent to restrict the volume flow rate of the fluid within the second segment 74b of the fluid flow path 74 to vary the heat supplied or heat removed from the flexible covering 70. In embodiments with more than one flexible covering 70, heat transfer provided by flexible coverings 70 may be individually controlled relative to one another and/or relative to one or more of the temperature zones 92a-92d defining the patient support portion 56.

The methods by which the patient temperature management system 30 provides for improved control of the microclimate will now be described. In certain embodiments, the thermal transfer device 32 includes one or more sensors 96. The sensors 96 may be coupled to the patient support portion 56 and/or the flexible covering 70. The sensors 96 measure pressure, temperature, and/or humidity, particularly at or near an interface between the thermal transfer device 32 and the patient P. The sensors 96 measuring pressure may detect the presence of the patient P within an area of the patient support portion 56, and/or an amount of pressure provided by the patient P supported on the patient support portion 56. In certain embodiments, the heat transfer associated with the temperature zones 92a-92d is altered based, at least in part, on a change in pressure as detected by the sensors 96. For example, the sensors 96 may detect the patient P moving one of his or her appendages A (e.g., outstretched from shoulder level to near the torso T). Based on the detected change of a location of the patient P on the patient support portion 56, the controller 90 may operate one or more of the pump 50, the energy transfer device 52, and the valves 86 to change the temperature or volume flow rate of the conditioned fluid within the fluid flow path 74 to alter the heat transfer of one or more of the temperature zones 92a-92d. In such an example, the heat transfer provided by the thermal transfer device 32 effectively "follows" the patient P. For another example, the sensors 96 may detect that the pressure from a portion of the patient P (e.g., the torso T) on the patient support portion 56 exceeds a predetermined pressure threshold. In response, the controller 90 may operate one or more of the pump 50, the energy transfer device 52, and the valves 86 to change the temperature or volume flow rate of the conditioned fluid within the fluid flow path 74 to alter the heat transfer within one or more of the temperature zones 92a-92d. Such an operation may be used, for example, to reduce the likelihood for pressure ulcers. In yet another example, the controller 90 may determine a measured distribution of pressure of the patient support portion 56. The controller 90 operates one or more of the pump 50, the energy transfer device 52, and the valves 86 to vary the heat supplied to or the heat removed from the temperature zones 92a-92d based on the measured distribution. The aforementioned exemplary methods directed to pressure-based control may be similarly extended to temperature, humidity, and other measurable environmental parameters.

In certain embodiments, the controller 90 operates one or more of the pump 50, the energy transfer device 52, and the valves 86 to vary the heat supplied to or the heat removed from the temperature zones 92a-92d based on a predetermined treatment protocol. The clinical presentation of the patient P may indicate a particular protocol of the thermal treatment, for example, cycling applications of hot and cold at fixed or varied intervals. The predetermined treatment protocol designed to provide the optimal thermal treatment may be stored within memory in communication with the controller 90. The predetermined treatment protocol may be selected on the user interface 94. Based on the selection of the predetermined treatment protocol, the controller 90 may operate one or more of the pump 50, the energy transfer device 52, and the valves 86 to change the temperature or volume flow rate of the conditioned fluid within the fluid flow path 74 to alter the heat transfer within one or more of the temperature zones 92a-92d to effectuate the predetermined treatment protocol.

In certain embodiments, the treatment protocol may be determined by the controller 90 based on the sensors 96 measuring pressure, temperature, and/or humidity. Based on the conditions at or near the interface between the patient P and the patient support portion 56, the controller 90 may prompt the user with the user interface 94 to initiate the treatment protocol most suitable to alleviate the parameters that may be deviating from within normal limits. In one example, the controller 90 automatically initiates the treatment protocol without prompting the user. In certain embodiments, the controller 90 is in communication with physiological monitoring equipment, including electrocardiography (ECG), electroencephalography (EEG), electromyography (EMG), galvanic skin response (GSR), capillary oxygen saturation ($SpO_2$), and continuous glucose monitoring (GCM), among others. Based on the physiological parameters received by the controller 90, the controller 90 may prompt the user or automatically initiate the treatment protocol to operate one or more of the pump 50, the energy transfer device 52, and the valves 86 to change the temperature or volume flow rate of the conditioned fluid within the fluid flow path 74 to alter the heat transfer within one or more of the temperature zones 92a-92d. Other closed-loop feedback control of the thermal transfer device 32 to provide the thermal treatment in real-time are within the scope of the present disclosure.

In certain embodiments previously described (see, for example, FIG. 3), the thermal transfer device 32 includes the flexible layer 57 removably coupled to and substantially conforming to at least a portion of the mattress 40 of the patient support apparatus 34 to define the patient support portion 56. The fasteners 59, such as elastic features coupled to or embedded within concertinaed fabric, may be provided to resiliently secure the flexible layer 57 of the thermal transfer device 32 to the mattress 40. The thermal transfer device 32 may substantially encase the mattress 40 or another mattress pad (e.g., a mattress overlay or mattress topper) situated on the patient support deck 38 or the mattress 40. According to further exemplary embodiments of the patient temperature management system 30 of the present disclosure, certain features of the thermal transfer device 32 are integrated into a mattress cover 100 (see FIG. 6A) of the mattress 40. As mentioned, the mattress 40 may be disposed on the patient support deck 38 of the patient support apparatus 34 (see FIG. 1).

Figure 6A:
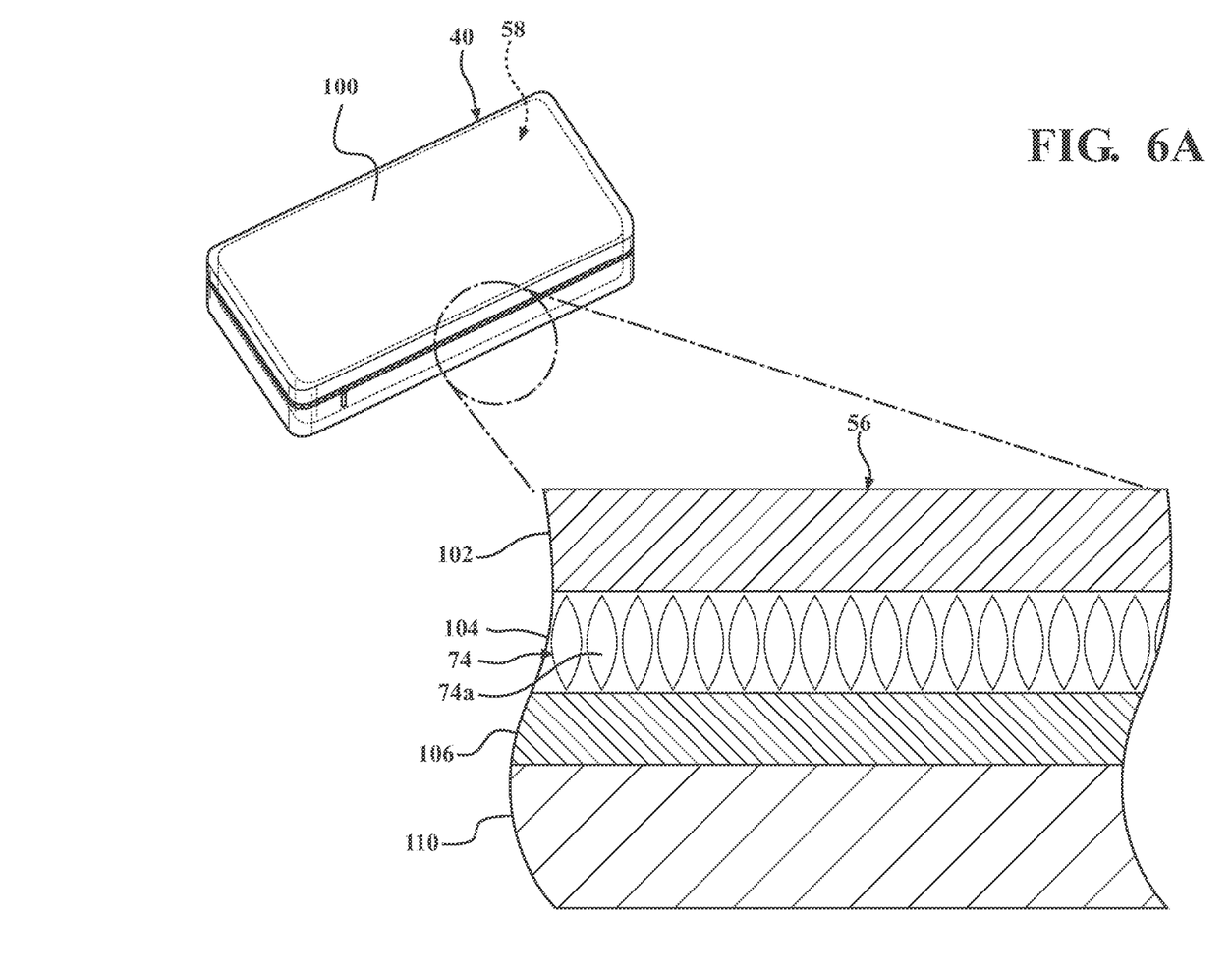
FIG. 6A is a perspective view of a mattress with a detailed sectional view of a mattress cover in accordance with an exemplary embodiment of the present disclosure.
Figure 6B:
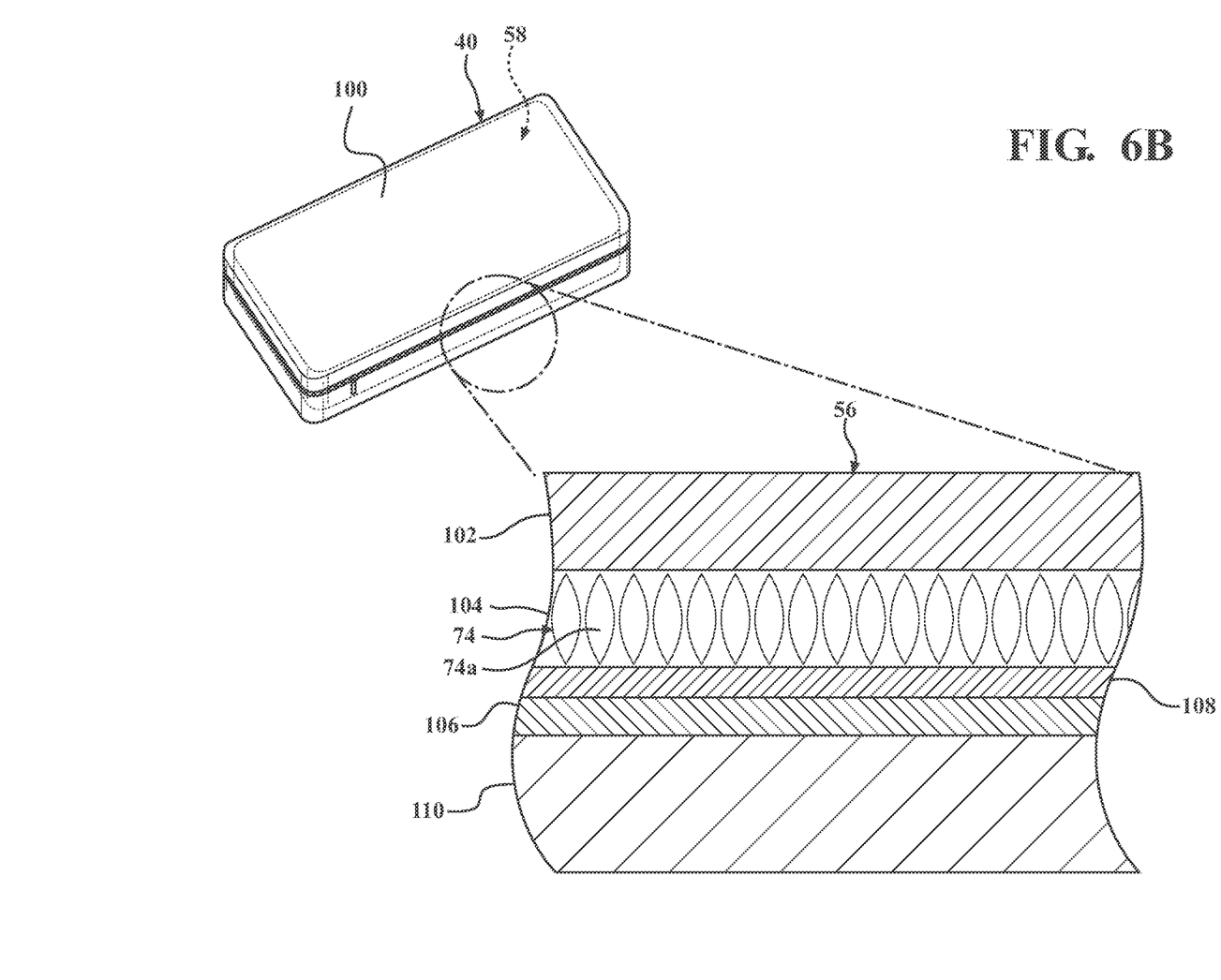
FIG. 6B is a perspective view of the mattress of FIG. 6A with a detailed sectional view of a mattress cover in accordance with another exemplary embodiment of the present disclosure.

Referring to FIGS. 6A and 6B, the mattress 40 is shown with detailed sectional views of two exemplary embodiments of the mattress cover 100. The mattress cover 100 may be coupled to the mattress 40 so as to cover the upper surface 58 of the mattress 40, and more particularly substantially encase the mattress 40. The mattress cover 100 includes a cover layer 102 that defines the patient support portion 56 supporting and contacting the patient P requiring the thermal treatment. Thus, absent bedding and the like, the patient P is supported by and in contact with the cover layer 102 of the mattress cover 100. In one example, the cover layer 102 is formed primarily from polyurethane, but other suitable materials are contemplated. The flexible covering 70, as described throughout the present disclosure, is adapted to be coupled to the cover layer 102.

The mattress cover 100 includes a fluid circulation layer 104 disposed within the mattress 40 and in direct contact with the cover layer 102. The first segment 74a of the fluid flow path 74 is disposed within the fluid circulation layer 104. In the present embodiment of FIGS. 6A and 6B, the first segment 74a of the fluid flow path 74 supplies heat to or removes heat from the cover layer 102 contacting and supporting the patient P. Adjacent materials may be RF welded with channels between the adjacent materials to construct the fluid circulation layer 104. The first segment 74a of the fluid flow path 74 is in fluid communication with the second segment 74b of the fluid flow path 74 associated with the flexible covering 70 coupled to the cover layer 102.

An inner membrane layer 106 may be provided within the mattress 40. The inner membrane layer 106 may be considered a layer of the mattress cover 100 or alternatively a layer of the mattress 40. In one example, the inner membrane layer 106 is in fluid communication with a source of air (not shown) that is moved through the inner membrane layer 106 to control humidity within the mattress cover 100. For example, controlling humidity within the mattress cover 100 consequently controls the humidity at the patient support portion 56 associated with the cover layer 102. In the exemplary embodiment of FIG. 6A, the inner membrane layer 106 is in direct contact with the fluid circulation layer 104. In the exemplary embodiment of FIG. 6B, a fire barrier layer 108 may be disposed within the mattress 40 and positioned intermediate the fluid circulation layer 104 and the inner membrane layer 106. One exemplary fire barrier layer 108 suitable for the present application is provided under the tradename NoMex (DuPont Company, Wilmington, Dela.). The mattress 40 includes a mattress cover layer 110 that may be disposed in direct contact with the inner membrane layer 106. The mattress cover layer 110 may be formed of foam or other materials, or combinations thereof. In one example, the structure of the mattress cover layer 110 takes the form of honeycombs that are adapted to resiliently buckle when supporting the patient P on the cover layer 102 of the mattress 40.

In certain embodiments, the mattress cover 100 includes a self-healing layer in direct contact with the cover layer 102, for example, positioned within the cover layer 102 or intermediate the cover layer 102 and the fluid circulation layer 104. The self-healing layer may be formed from a low-durometer poured urethane with the capability of self-sealing in the event of small, inadvertent punctures from sharps. It is to be understood that the aforementioned features of the mattress cover 100 may additionally or alternatively be included in the flexible layer 57 of the thermal transfer device 32. For example, the flexible layer 57 (see FIG. 3) of the thermal transfer device 32 includes the fluid circulation layer 104 in direct contact with the cover layer 102 with the flexible covering 70 being coupled to the cover layer 102. The flexible layer 57 may also include the self-healing layer in direct contact with the cover layer 102.

One readily apparent advantage of the thermal transfer device 32 described throughout the present disclosure is facilitation of eased coupling and decoupling of the thermal transfer device 32 with the patient P supported on the patient support apparatus 34. With the flexible covering 70 movable relative to the patient support portion 56 to define the space 72 therebetween, the portion of the patient P substantially surrounded by the thermal transfer device 32 does not need to be moved during coupling and decoupling. Conventional sleeves require the patient's appendages be lifted or the patient turned in order to wrap the sleeve around the portion of the patient. The moving of the patient is laborious, cumbersome, and potentially injurious to the patient.

Figure 7:
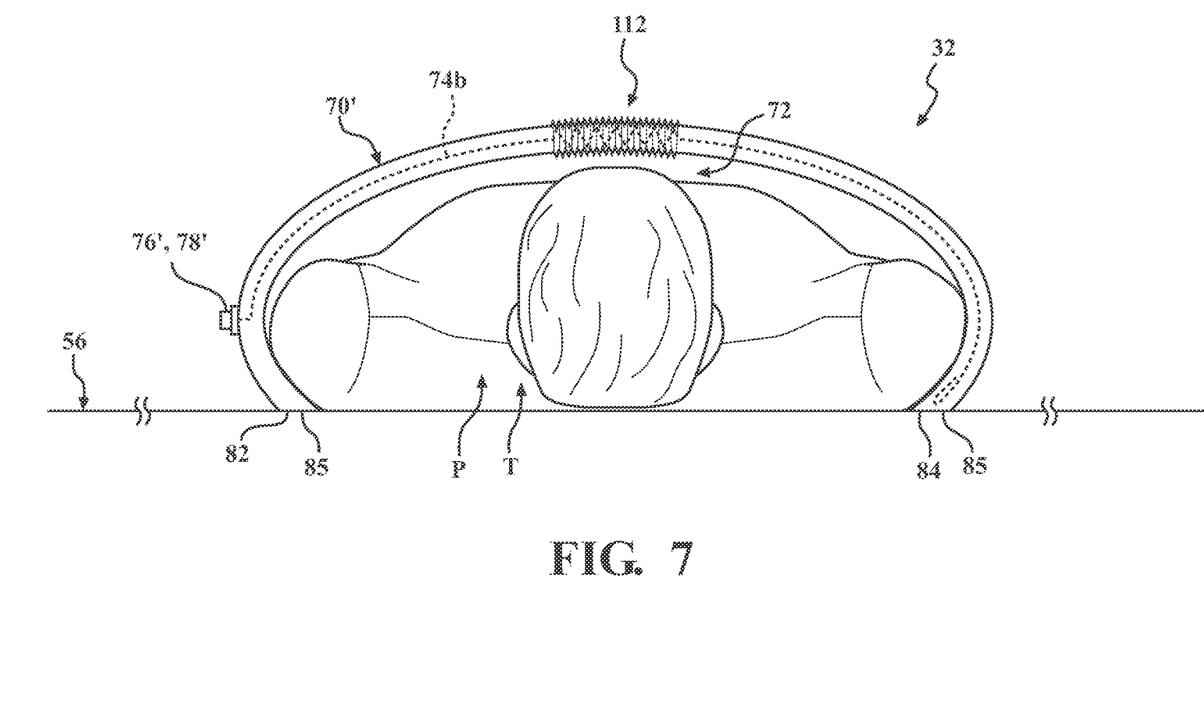
FIG. 7 is an elevation view of a thermal transfer device in accordance with another exemplary embodiment of the present disclosure with the patient supported on the patient support portion of the thermal transfer device.

In accordance with another exemplary embodiment of the thermal transfer device 32 shown in FIG. 7, the flexible covering 70' comprises the first end 82 opposite the second end 84. Both of the first and second ends 82, 84 are removably coupled to the patient support portion 56 to define the space 72 therebetween. As shown in FIG. 7, when both the first and second ends 82, 84 are coupled to the patient support portion 56, the flexible covering 70' receives and substantially conforms to a portion of the patient P. The fluid flow path 74, in particular the second segment 74b, is within the flexible covering 70' to receive the conditioned fluid from the fluid source 46 for providing the thermal treatment.

As previously described with reference to FIGS. 1-5, the thermal transfer device 32 includes the inlet 76 and the outlet 78 arranged to circulate the conditioned fluid from the fluid source 46 through said fluid flow path 74 for supplying heat to or removing heat from the flexible covering 70. The inlet 76 and the outlet 78 are coupled to the patient support portion 56 with the second segment 74b of the fluid flow path 74 in communication with the first segment 74a of the fluid flow path 74. Based on the manner to be described in which the flexible covering 70' of the present embodiment couples with the patient support portion 56, an inlet 76' and an outlet 78' separate from the inlet 76 and the outlet 78 of previously described embodiments may be provided with the inlet 76' and the outlet 78' disposed on the flexible covering 70'.

The flexible covering 70' includes fasteners 85 disposed at each of the first and second ends 82, 84. The fasteners 85 removably couple the first and second ends 82, 84 of the flexible covering 70' to the patient support portion 56. For examples, the fasteners 85 is one of adhesive and hook and eye connections. In other examples, the fasteners 85 include zippers, buttons, snaps, and the like. Adhesive and hook and eye connections are particularly advantageous in the present embodiment because the first and second ends 82, 84 of the flexible covering 70' may be interposed between the patient P and the patient support portion 56 when the flexible covering 70' is coupled to the patient support portion 56. Consequently, the weight of the patient P compresses the fasteners 85 against the patient support portion 56. FIG. 7 shows the first and second ends 82, 84 positioned intermediate the torso T of the patient P and the patient support portion 56. The thin profiles of adhesive and hook and eye connections relative to, for example, buttons and snaps, minimizes potential pressure points for the patient P.

With the flexible covering 70' coupled to the patient support portion 56, the first and second ends 82, 84 may be spaced apart and separated by a portion of the patient support portion 56. As shown in FIG. 7, the first and second ends 82, 84 are generally situated opposite the torso T of the patient P. The arrangement results in the center of the torso T directly contacting the patient support portion 56, the anatomy applying the most pressure to the patient support portion 56. Increased comfort for the patient P may be realized with the first and second ends 82, 84 beneath only the anatomy of the patient P applying less pressure to the patient support portion 56. It is also contemplated that in certain embodiments, the flexible covering 70' may surround the patient P to collectively cover the appendages A and the torso of the patient P. In such an embodiment, the flexible covering 70' may be open at the head end 64 and closed at the foot end 66 with the head of the patient P positioned external to the flexible covering 70' surrounding the patient P (e.g., akin to a sleeping bag). In another example, the flexible covering 70' may be open at the head end 64 and the foot end 66 with the head and feet of the patient P positioned external to the flexible covering 70' surrounding the patient P.

In certain embodiments, the flexible covering 70' is formed from elastic material to accommodate patients of different sizes. Further, the flexible covering 70' may include concertinaed material 112 intermediate the first and second ends 82, 84, as shown in FIG. 7. The concertinaed material 112 is adapted to expand to accommodate and substantially conform to the portion of the patient P when the first and second ends 82, 84 are coupled to the patient support portion 56. In one example, the concertinaed material 112 is positioned adjacent the patient P opposite the first and second ends 82, 84 when the first and second ends 82, 84 are coupled to the patient support portion 56. At least a portion of the fluid flow path 74, in particular the second segment 74b, extends through the concertinaed material 112. The fluid flow path 74 may also be adapted to expand along with the concertinaed material 112. In one example, at least the portion of the fluid flow path 74 extending through the concertinaed material 112 may be formed from resilient tubing. Additionally or alternatively, at least the portion of the fluid flow path 74 extending through the concertinaed material 112 may be concertinaed as well. It is to be understood that the elastic and/or concertinaed material 112 providing comfort to the patient P may be incorporated with the flexible covering 70 of the previously described embodiments.

In addition to increased patient comfort, the flexible coverings 70, 70' may be easily coupled and decoupled. The flexible layer 57 defining the patient support portion 56 is positioned on the mattress 40 disposed on the patient support apparatus 34. The patient P is positioned on the flexible layer 57 (or the cover layer 102 of the mattress cover 100). The flexible covering 70, 70' is moved relative to the patient support portion 56 to provide the space 72 between the flexible covering 70, 70' and the patient support portion 56. In one example, the first end 82 is fixedly coupled to the patient support portion 56 on one side of the patient P, and the second end 84 is moved about a portion of the patient P and coupled to the patient support portion 56 on the other side of the patient P. In another example, the first and second ends 82, 84 are coupled to the patient support portion 56 on opposing sides of the patient P with the first and second ends 82, 84 interposed between the patient P and the patient support portion 56 such that the weight of the patient P compresses the fasteners 85 against the patient support portion 56. The flexible covering 70, 70' defining the space 72 receives and substantially conforms to the portion of the patient P. Thermal treatment may be provided in manners previously described with conditioned fluid being directed from the fluid source 46 through the fluid flow path 74 to supply heat to or remove heat from the flexible layer 57 (or the cover layer 102 of the mattress cover 100) and the flexible covering 70, 70' in thermal communication with the patient P.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject-matter of a claim dependent from one independent claim can also be implemented in connection with another independent claim.

What is claimed is:

1. A thermal transfer device comprising:
   a patient support portion adapted to support and contact a patient requiring thermal treatment with the patient support portion defining a first segment of a fluid flow path to receive a fluid from a fluid source for providing the thermal treatment;
   a flexible covering coupled to the patient support portion and movable relative to the patient support portion to define a space therebetween adapted to receive and substantially conform to a portion of the patient with the flexible covering defining a second segment of the fluid flow path to receive the fluid from the fluid source for providing the thermal treatment; wherein the first and second segments of the fluid flow path are continuous and are arranged in a tortuous configuration; and
   an inlet and an outlet arranged to circulate the fluid from the fluid source through the fluid flow path for supplying heat to or removing heat from the patient support portion and the flexible covering.

2. The thermal transfer device of claim 1, further comprising a flexible layer adapted to be removably coupled and substantially conform to a portion of a mattress with the flexible layer comprising the patient support portion and with the flexible covering coupled to the flexible layer.

3. The thermal transfer device of claim 2, wherein a portion of the flexible covering is fixedly coupled to the flexible layer.

4. The thermal transfer device of claim 2, wherein the flexible layer further comprises a fluid circulation layer in direct contact with a cover layer to define the patient support portion, the fluid flow path disposed within the fluid circulation layer and adapted to receive the fluid for supplying heat to or removing heat from the cover layer, and the flexible covering being coupled to the cover layer.

5. The thermal transfer device of claim 1, wherein the second segment of the fluid flow path is devoid of a port.

6. The thermal transfer device of claim 1, wherein the patient support portion and the flexible covering comprise counterposing couplers adapted to removably couple the patient support portion and the flexible covering.

7. The thermal transfer device of claim 6, wherein the counterposing couplers further comprise a plurality of counterposing couplers arranged at positions spaced apart on the patient support portion such that the thermal transfer device is configurable between multiple configurations comprising the flexible covering being coupled at one of the positions.

8. The thermal transfer device of claim 1, further comprising a fluid circulation system comprising valves adapted to restrict flow of the fluid within the fluid flow path and a controller in communication with the valves; and wherein the controller is adapted to operate the valves to selectively route flow of the fluid within the fluid flow path.

9. The thermal transfer device of claim 8, wherein the patient support portion is defined by temperature zones each comprising a portion of the patient support portion with the controller adapted to operate the valves to selectively route the fluid to two or more of the temperature zones to vary the heat supplied to or heat removed from the temperature zones.

10. The thermal transfer device of claim 9, further comprising sensors coupled to the patient support portion and in communication with the controller with the sensors configured to measure one of pressure, temperature, and humidity, wherein the controller is adapted to operate the valves to vary the heat supplied to or heat removed from the temperature zones based on a measured distribution of the one of pressure, temperature, and humidity of the patient support portion.

11. The thermal transfer device of claim 10, wherein the fluid circulation system further comprises a pump in fluid communication with the fluid flow path and in communication with the controller and adapted to circulate the fluid from the fluid source through the fluid flow path with the controller adapted to operate the pump to selectively adjust a flow rate of the fluid within the fluid flow path to vary the heat supplied to or heat removed from the temperature zones.

12. The thermal transfer device of claim 9, further comprising sensors coupled to the patient support portion and in communication with the controller with the sensors configured to measure one of pressure, temperature, and humidity, wherein the controller is adapted to operate the valves to vary the heat supplied to or heat removed from the temperature zones based on a predetermined treatment protocol.

13. The thermal transfer device of claim 12, wherein the fluid circulation system further comprises a pump in fluid communication with the fluid flow path and in communication with the controller and adapted to circulate the fluid from the fluid source through the fluid flow path with the controller adapted to operate the pump to selectively adjust a flow rate of the fluid within the fluid flow path to vary the heat supplied to or heat removed from the temperature zones.

14. The thermal transfer device of claim 9, wherein the fluid circulation system further comprises an energy transfer device in fluid communication with the fluid flow path and in communication with the controller, wherein the controller is adapted to operate the energy transfer device to selectively adjust temperature of the fluid within the fluid flow path to vary the heat supplied to or heat removed from the temperature zones.

15. The thermal transfer device of claim 1, wherein the patient comprises appendages extending from a torso, and with the space defined between the flexible covering and the patient support portion being adapted to receive and substantially conform to one of the appendages or the torso of the patient.

16. The thermal transfer device of claim 15, wherein the flexible covering comprises a pair of flexible coverings with each of the flexible coverings and the patient support portion defining the space adapted to receive and substantially conform to the appendages of the patient.

17. The thermal transfer device of claim 15, wherein the flexible covering comprises a pair of flexible coverings detachably coupled to one another with the flexible coverings and the patient support portion defining the space adapted to receive and substantially conform to the torso of the patient.

18. The thermal transfer device of claim 1, wherein the flexible covering includes a first end opposite a second end with both of the first and second ends adapted to be removably coupled to the patient support portion to define the space therebetween.

19. The thermal transfer device of claim 18, further comprising fasteners disposed at each of the first and second ends with the fasteners adapted to removably couple the first end and the second end of the flexible covering to the patient support portion.

* * * * *